United States Patent [19]
Slater

[11] Patent Number: 5,819,738
[45] Date of Patent: Oct. 13, 1998

[54] JAW ASSEMBLY HAVING PROGRESSIVELY LARGER TEETH AND ENDOSCOPIC BIOPSY FORCEPS INSTRUMENT INCORPORATING SAME

[75] Inventor: Charles R. Slater, Fort Lauderdale, Fla.

[73] Assignee: Symbiosis Corporation, Miami, Fla.

[21] Appl. No.: 675,078

[22] Filed: Jul. 3, 1996

[51] Int. Cl.⁶ .................................................. A61B 17/28
[52] U.S. Cl. ........................... 128/751; 606/205; 606/207
[58] Field of Search ................... 128/751, 753, 128/754; 606/45, 46, 51, 52, 205, 206, 207, 208

[56] References Cited

U.S. PATENT DOCUMENTS

| | | | |
|---|---|---|---|
| 3,404,683 | 10/1968 | Eizenberg | 606/207 |
| 3,895,636 | 7/1975 | Schmidt | 128/305 |
| 4,880,015 | 11/1989 | Nierman | 128/751 |
| 5,133,727 | 7/1992 | Bales et al. | 606/170 |
| 5,228,451 | 7/1993 | Bales et al. | 128/751 |
| 5,366,477 | 11/1994 | LeMarie, III et al. | 606/208 |
| 5,394,885 | 3/1995 | Francese | 128/751 |
| 5,395,375 | 3/1995 | Turkel et al. | 606/83 |
| 5,507,296 | 4/1996 | Bales et al. | 128/751 |
| 5,553,624 | 9/1996 | Francese et al. | 606/207 |
| 5,613,499 | 3/1997 | Palmer et al. | 606/207 |

FOREIGN PATENT DOCUMENTS

| | | | |
|---|---|---|---|
| 1743593 | 6/1992 | U.S.S.R. | 606/205 |

*Primary Examiner*—Vincent Millin
*Assistant Examiner*—V. Srivastava
*Attorney, Agent, or Firm*—David P. Gordon; David S. Jacobson

[57] ABSTRACT

An endoscopic forceps jaw assembly for an endoscopic instrument includes a pair of articulating opposed jaws each having a jaw cup. The jaw cups are provided with teeth which increase in height from the proximal end of the jaw cup to the distal end. The jaws are rotatable relative to each other about a common axis and define an open position and a closed position. When the jaws are rotated toward the closed position, the teeth interleave substantially simultaneously. An endoscopic instrument utilizing the jaws of the invention is also provided and further includes an actuation handle, a tubular member, and a control member. The jaw assembly is coupled to the distal end of the control member and rotatably coupled to the distal end of the tubular member, such that the pair of articulable opposed jaws open and close by rotating in response to movement of the control member relative to the tubular member. The jaws may also be electrically conductive and coupled to an electrocautery voltage supply.

17 Claims, 3 Drawing Sheets

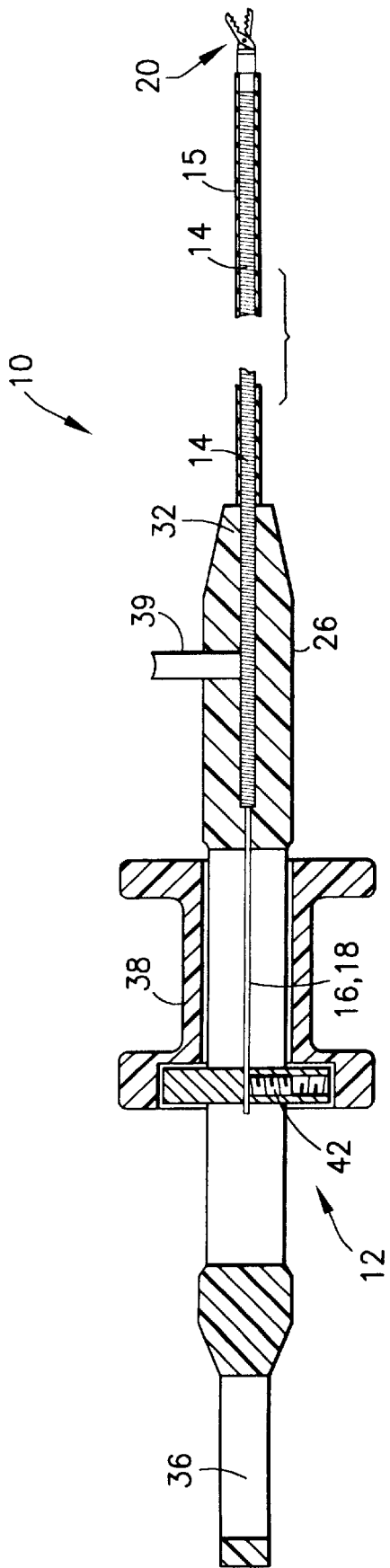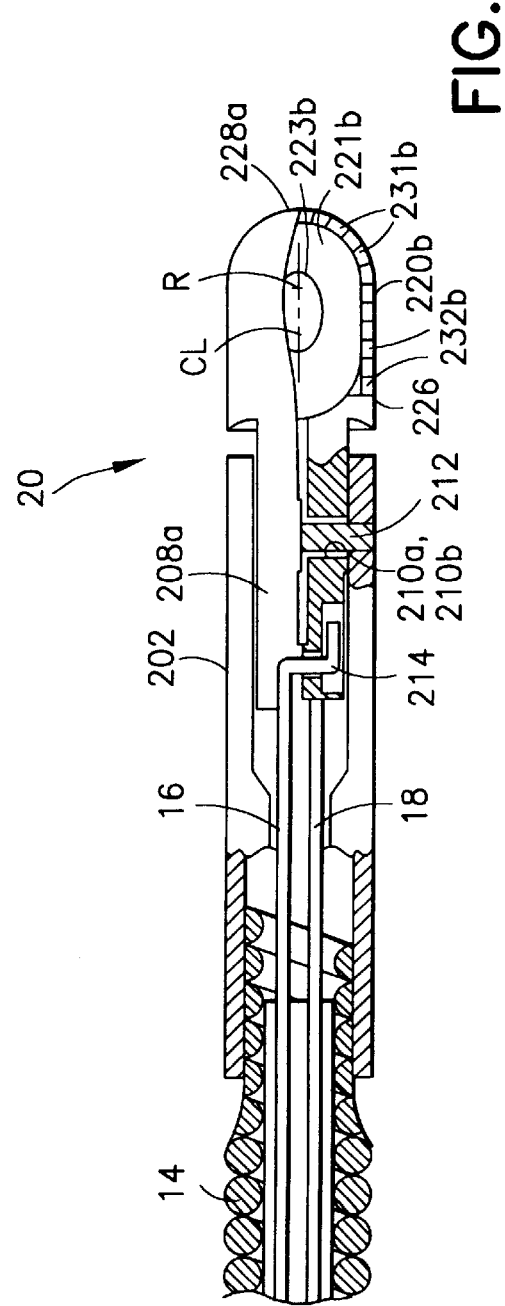

JAW ASSEMBLY HAVING PROGRESSIVELY LARGER TEETH AND ENDOSCOPIC BIOPSY FORCEPS INSTRUMENT INCORPORATING SAME

BACKGROUND OF THE INVENTION

1. Field of the Invention

The invention relates to endoscopic instruments. More particularly, the invention relates to biopsy forceps jaws. For purposes herein, the term "endoscopic" is to be understood in its broad sense to include laparoscopic, arthroscopic, and other microsurgical instruments whether or not used with an endoscope.

2. State of the Art

Endoscopic biopsy forceps are used for taking tissue samples from the human body for analysis. These forceps typically have a pair of generally hemispherical cupped jaws attached to both the distal end of a long flexible coil, and the distal end of an actuating means which opens and closes the jaws when the actuating means is manipulated by the practitioner. The endoscopic biopsy procedure is accomplished through an endoscope which is inserted into a body and guided by manipulation to the biopsy site. The endoscope typically includes a long narrow flexible tube carrying distal optical means and having a narrow lumen for receiving the biopsy forceps. The practitioner guides the endoscope to the biopsy site using the optical means and inserts the forceps, with jaws closed, through the lumen of the endoscope to the biopsy site. While viewing the biopsy site through the optical means of the endoscope, the practitioner opens the forceps jaws and carefully guides the jaws around a tissue to be sampled. When the jaws are in the correct position, the practitioner manipulates the actuating means and closes the jaws on the tissue to be sampled. The cupped jaws sever or grip a sample of the tissue in the space between the cupped jaws so that the sample may be removed (ripped away) from the biopsy site. The forceps are then withdrawn from the lumen of the endoscope while the jaws are kept shut, with the sample captured in the space between the cupped jaws.

The endoscopic biopsy procedure poses several challenges to the design and manufacture of the biopsy forceps instrument and particularly the biopsy forceps jaws. The jaws must be small enough to fit through the narrow lumen of the endoscope, yet strong enough and/or sharp enough to cut and/or tear tissue. An early example of an endoscopic biopsy forceps instrument is shown in U.S. Pat. No. 3,895,636 to Schmidt. The forceps in Schmidt include a pair of cupped toothless jaws with sharpened opposed edges intended to cut through tissue being sampled. Due to the miniature size of the jaws, however, it is difficult to sharpen the edges to a very high degree. Consequently, it is necessary to apply great force to the jaws in order to sever the tissue being sampled. In practice, sufficient force to sever the tissue is rarely achieved. Thus, either the jaws effect a clamping action which permits the tissue to be torn away from the biopsy site, or the jaws simply slip off the tissue without cutting or tearing it.

U.S. Pat. No. 4,880,015 to Nierman shows an endoscopic biopsy forceps instrument having opposed rectangularly cupped jaws with teeth on their parallel edges. When the jaws close, opposed teeth interleave providing a slightly better gripping ability than the jaws disclosed by Schmidt. However, the rectangular configuration of the jaws and the absence of teeth at the distal end of the jaws limits their functionality. Additionally, with these jaws and other toothed jaws, the teeth often do not align properly and prevent the jaws from closing completely which adds to the inefficiency of cutting and/or tearing and resultant slippage. Similarly, the misalignment of the opposed teeth sometimes causes the jaws to lock in the closed position.

Co-owned U.S. Pat. No. 5,228,451 to Bales et al., the complete disclosure of which is hereby incorporated by reference herein, discloses an endoscopic biopsy forceps instrument having a pair of opposed jaws with teeth which extend along an arced (radial) outer edge of each jaw. The teeth are offset by one-half pitch relative to the longitudinal center line of the jaw so that the upper jaw and lower jaw can be made from the same mold and still permit the teeth to align (interleave) when the jaws are closed. This arrangement of jaw teeth greatly improves the cutting and/or gripping (tearing) action of the forceps. However, even with these biopsy forceps it is noted that the jaws cannot adjust or compensate for the nonsimultaneous closing of the jaw teeth which occur due to the rotation of the opposing jaws. In particular, the teeth at the proximal end of the rotating jaw arrangement close before the teeth at the distal end of the jaw arrangement, often resulting in the uneven gripping and/or cutting of a tissue sample or even the inability of the distal end of the jaws to close. This may also lead to incomplete cauterization when the jaws of the biopsy forceps instrument are electrified.

SUMMARY OF THE INVENTION

It is therefore an object of the invention to provide endoscopic forceps jaws having teeth which are arranged along the jaws and which close substantially simultaneously as the jaws rotate from an open to a closed position.

It is another object of the invention to provide endoscopic forceps jaws having a plurality of teeth arranged along the length of the jaws and increasing in height from the proximal end of the jaws to the distal end of the jaws.

It is a further object of the invention to provide a bipolar cautery endoscopic forceps jaws having two opposed conducting jaws with teeth which are arranged along each jaw to allow for the even conduction of electricity between the jaws.

It is an additional object of the invention to provide an endoscopic biopsy forceps instrument which incorporates the jaws of the invention.

In accordance with the objects of the invention, which will be discussed in detail below, an endoscopic forceps jaw assembly for an endoscopic instrument includes a pair of articulable opposed jaws rotatable relative to each other about a common axis. Each jaw has an array of teeth on each side of the jaw. Each array of teeth is arranged such that the teeth in the array progressively increase in height from the shorter proximal teeth to the taller distal teeth of the jaw. In a preferred arrangement, the peaks of the teeth of an array fall along a first straight line and the valleys of the same teeth fall along a second straight line which diverges from the first line. When the jaws are rotated about the clevis from an open position toward a closed position, all of the teeth of the respective jaws interleave substantially simultaneously. In other words, the jaws are arranged such that the peaks of the smaller proximal teeth and the peeks of the larger distal teeth rotate through the imaginary mid-plane of the jaws of the biopsy forceps instrument.

The endoscopic instrument of the present invention broadly includes an actuation handle, a tubular member, a control member, and a jaw assembly. The tubular member which is often a coil preferably includes a distally positioned clevis means. The control member (typically a wire) extends through the tubular member. The actuation handle includes a stationary member, coupled to the proximal end of either the control member or the tubular member, and a movable member coupled to the proximal end of the other of the control member and the tubular member, such that moving the movable member relative to the stationary member imparts movement of the control member relative to the tubular member. The jaw assembly is coupled to the distal end of the control member and rotatably coupled to the clevis means, such that the pair of articulable opposed jaws open and close by rotating about the clevis means in response to movement of the control member relative to the tubular member.

Additional objects and advantages of the invention will become apparent to those skilled in the art upon reference to the detailed description taken in conjunction with the provided figures.

BRIEF DESCRIPTION OF THE DRAWINGS

FIG. 1 is a side elevational view in section of the biopsy forceps instrument of the invention;

FIG. 3 is a partially cut away plan view of the distal end of the biopsy forceps instrument of FIG. 1 with the biopsy forceps jaws in the closed position;

DETAILED DESCRIPTION OF THE PREFERRED EMBODIMENTS

Figure 2:
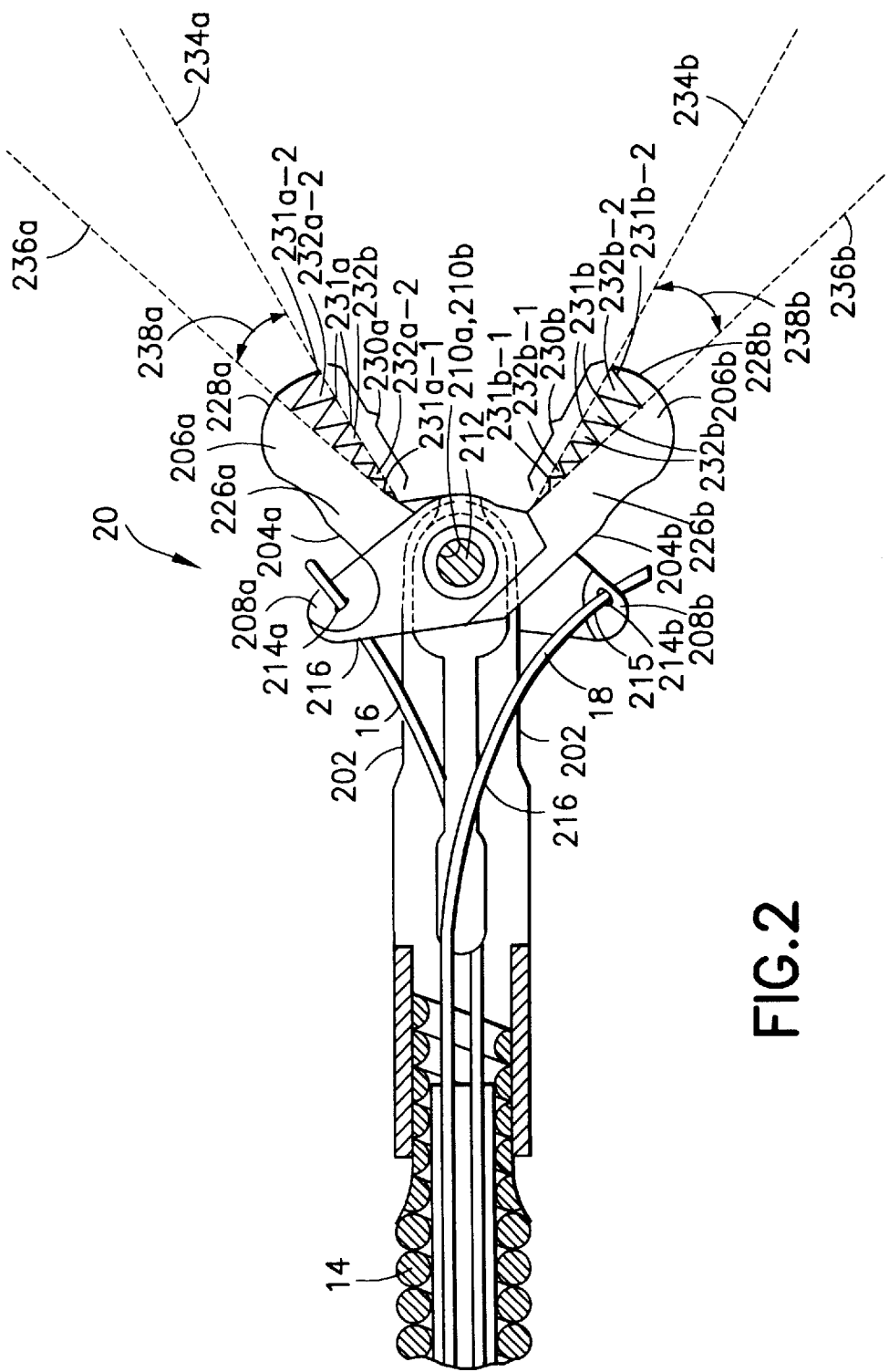
FIG. 2 is a side elevational view of the distal end of the biopsy forceps instrument of FIG. 1 with the biopsy forceps jaws in the open position.

Referring to FIGS. 1 and 2, the preferred endoscopic instrument of the present invention broadly includes an actuation handle 12, a coil 14, a control member or control wires 16, 18, and a jaw assembly 20. The control wires 16, 18 extend through the coil 14. The actuation handle 12 includes a stationary member 26 having a thumb ring 36, and a spool 38. The stationary member 26 is coupled to the proximal end of the coil 14 and the spool 38 is coupled to the proximal end of the control wires 16, 18, such that moving the spool 38 relative to the stationary member 26 imparts movement of the control wires relative to the coil. The coil is covered with an insulative sheath 15, such as an FEP sheath. A cautery plug 39, for coupling to a cautery means, enters the stationary member 26 laterally and is conductively coupled to the coil 14. The jaw assembly 20 includes a pair of preferably identical articulating opposed jaws 204a, 204b and a clevis 202. The clevis 202 is coupled to the distal end of the coil 14. The jaws 204a, 204b are coupled to the distal end of the control wires 16, 18 and are also rotatably coupled to the clevis 202, such that the jaws open and close by rotating about the clevis 202 in response to movement of the control wires 16, 18 relative to the coil 14. Actuation and movement of the control wires relative to the coil is described more fully in co-owned U.S. Pat. No. 5,228,451 to Bales et al.

As seen in FIG. 2, each identical jaw 204a, 204b has a distal toothed cup portion 206a, 206b, a proximal tang 208a, 208b, and a transverse mounting bore 210a, 210b. The jaws are mounted on the clevis 202 by a pin 212 which passes through the mounting bores 210a, 210b of the jaws. The proximal tang 208a, 208b of each jaw is also provided with a bore 214a, 214b which receives the distal end 215, 216 of one of the control wires 16, 18.

Figure 4:
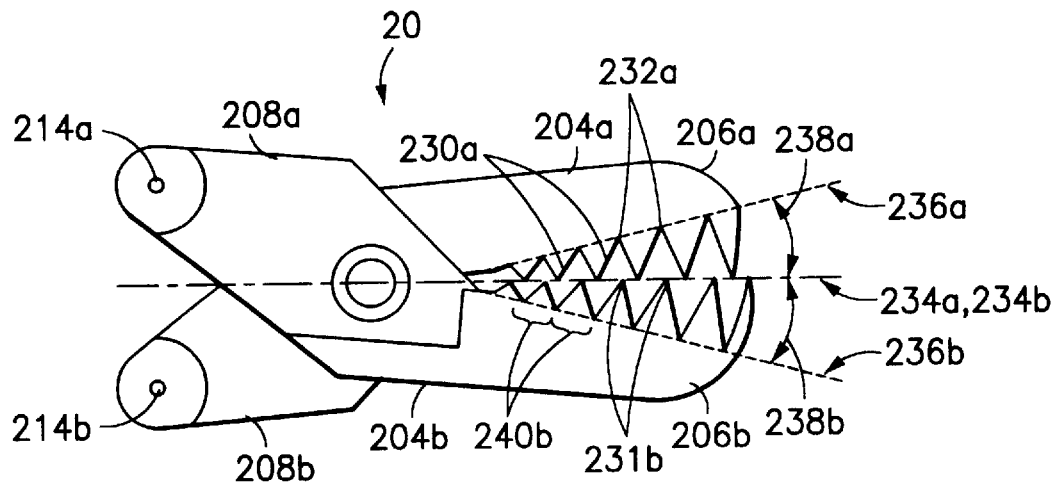
FIG. 4 is a side elevational view of the distal end of the biopsy forceps instrument of FIG. 1 with the biopsy forceps jaws in the partially open position.

As best illustrated in FIGS. 2, 3 and 4, the distal toothed cup portion 206a, 206b of the jaw 204a, 204b is preferably an oblate hemispherical member having a rim 220a, 220b, a hollow interior 221a, 221b, and an optional fenestration hole 223a, 223b at the bottom of the hollow interior. The rim 220a, 220b has an array of triangular teeth 230a, 230b defined by valleys 232a, 232b and by peaks 231a, 231b. As can be seen in FIG. 4, the peaks 231a, 231b vary in height and the valleys 232a, 232b vary in depth depending on their position along the rim 220a, 220b of the cup portion 206a, 206b. In particular, the peaks 231a, 231b increase in height and the valleys 232a, 232b increase in depth from the proximal end 226a, 226b of the cup portion to the distal end 228a, 228b of the cup portion 206a, 206b, such that the shortest peaks 231a-1, 231b-1 and shallowest valleys 232a-1, 232b-1 are at the proximal end of the cup portion and the tallest peaks 231a-2, 231b-2 and deepest valleys 232a-2, 232b-2 are at the distal end of the cup portion. The progressively taller peaks and deeper valleys thus form progressively larger teeth 230a, 230b. Referring to FIGS. 2 and 4, it will be appreciated that a first plane 234a, 234b is defined by joining the peaks 231a, 231b of each jaw 204a, 204b, and a second plane 236a, 236b is defined by joining the valleys 232a, 232b of each jaw 204a, 204b. In a preferred embodiment of the invention, the triangular teeth 230a, 230b, from the shortest to the tallest, preferably have equal base widths 240a, 240b (See FIG. 4).

As exemplified in FIG. 3, in accord with a preferred aspect of the invention, the teeth 230a, 230b at the curved distal end 228a, 228b of the cup portion 206a, 206b are radially arranged about a point "R" as described more fully in co-owned U.S. Pat. No. 5,228,451 to Bales et al. Additionally, the peaks 231a, 231b and valleys 232a, 232b one side of the longitudinal centerline "CL" of the cup 206a, 206b are preferably displaced by one half pitch from the peaks 231a, 231b and valleys 232a, 232b on the other side of the centerline of the cup 206a, 206b. This radial arrangement and half pitch displacement provides for self-alignment and the ability to use a single mold to make a pair of identical mating jaws as described in U.S. Pat. No. 5,228,451 to Bales et al.

Figure 5:
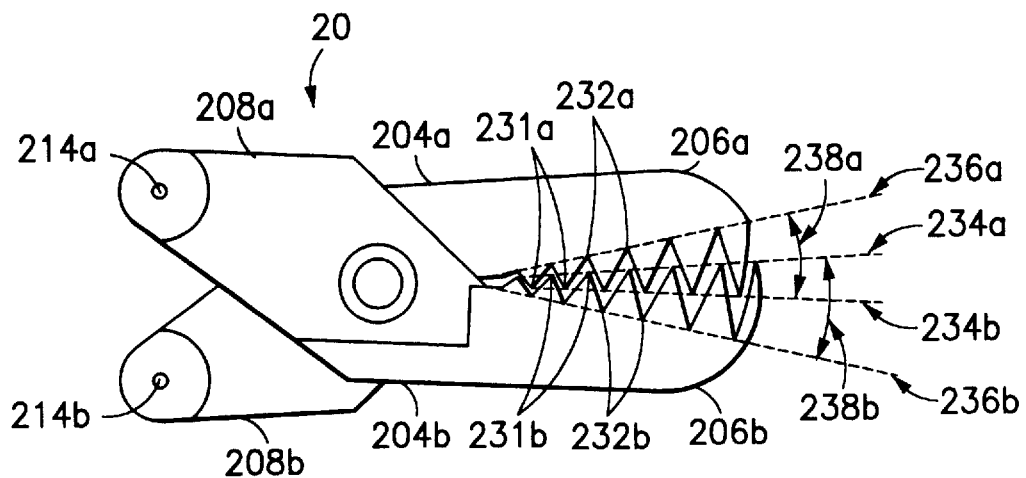
FIG. 5 is a side elevational view of the distal end of the biopsy forceps instrument of FIG. 1 with the biopsy forceps jaws in an almost closed position.
Figure 6:
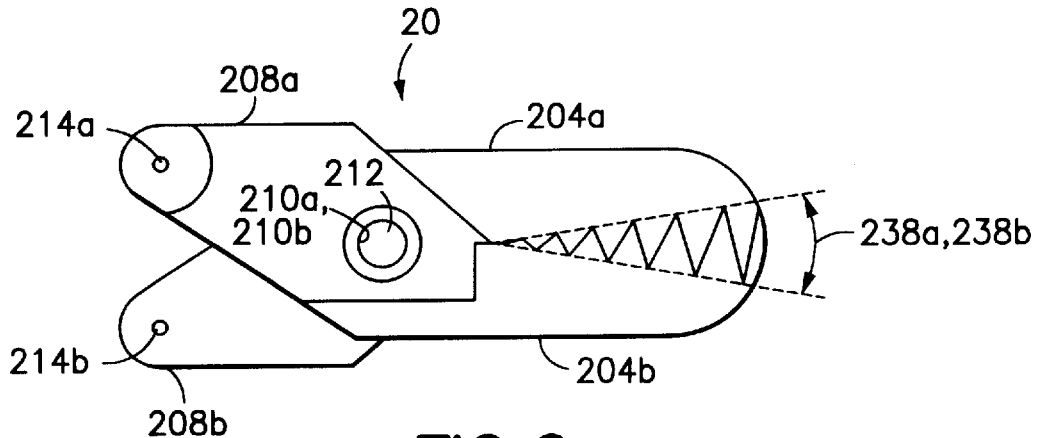
FIG. 6 is a side elevational view of the distal end of the biopsy forceps instrument of FIG. 1 with the biopsy forceps jaws in the closed position.

Referring to FIGS. 4, 5 and 6, the jaw assembly 20 is shown in the partially open, the almost closed and fully closed positions, respectively. FIG. 4 shows the jaws in the partially open position with the first planes 234a, 234b joining the peaks of the teeth of each jaw 204a, 204b being identical. It will be appreciated that when the plane 234a of jaw 204a is identical to the plane 234b of jaw 204b, none of the teeth from the jaws are touching or meshing. As seen in FIG. 5, as the jaws 204a, 204b of the jaw assembly 20 are urged toward one another toward a closed position, the teeth at the proximal ends 226a, 226b of the jaws 204a, 204b mesh at the same rate as the teeth at the distal ends 228a, 228b of the jaws 204a, 204b, moving through the same angle 238a, 238b. In particular, the peaks 231a, 231b of each jaw cup portion 206a, 206b close with the valleys 232a, 232b of the opposing jaw cup portion 206a, 206b simultaneously. In this manner, the jaw assembly 20 evenly grips and/or tears tissue samples from a biopsy site. FIG. 6 shows the jaw assembly 20 in the fully closed position, with the peaks 231a, 231b and valleys 232a, 232b forming the teeth 230a, 230b of each jaw 204a, 204b being fully meshed. As the jaws 204a, 204b are identical but with one side off pitch as discussed above, the jaw assembly 20 is properly aligned when closed and exhibits no gaps or irregularities. In addition, the evenly spaced closing results in a better electrical conductivity arrangement for forceps having cautery capabilities, as the proximal teeth do not engage each other prior to the distal teeth engaging. When the forceps close on thin and flat tissue, the cauterization of the tissue occurs along all of the teeth and at substantially the same time.

There have been described and illustrated herein a jaw assembly for an endoscopic biopsy forceps instrument where the teeth of the jaws become progressively larger (higher) according to their location on the jaw. While a particular embodiment of the invention has been described, it is not intended that the invention be limited thereto, as it is intended that the invention be as broad in scope as the art will allow and that the specification be read likewise. Thus, while particular types of jaws have been disclosed, it will be appreciated that other jaws may be used as well. For example, while a partly hemispherical hollow jaw has been disclosed, a non-hemispherical jaw may also be used. Furthermore, while particular shapes of teeth formed by the peaks and valleys have been disclosed, it will be understood that other shaped peaks and valleys can be used which will form other shaped teeth. In addition, while the base width of each tooth has been disclosed as being equal, it will be appreciated that the teeth formed by taller peaks and deeper valleys can be wider or narrower than the teeth formed by shorter peaks and shallower valleys. A variety of other geometries and dimensions may also be used for the teeth. Also, while the teeth are shown to have a progressive increase in size based upon the angle between the first plane and the second plane, it will be recognized that the peak heights and valley depths may increase in size based on a different angle between the two planes. It will be further understood that while no particular number of teeth is preferred, the number of teeth along the rim of the jaw cup may be varied.

Furthermore, while particular actuation and rotation means have been shown for opening and closing the jaw assembly, it will be understood that other actuation and/or rotation means can be similarly used. For example, while the coil has been disclosed as being coupled to the stationary member and the control wires coupled to the spool, it will be appreciated that the coil can be coupled to the spool and the control wire coupled to the stationary member. In addition, while the actuation handle has been generally disclosed as having a stationary member and a movable member movable axially relative to the stationary member, other actuation handles may be used. For example, a handle having a stationary member and a movable lever which acts via a pinion to move a rack axially relative the stationary member can be used with a similar coupling of the coil and control wires to the stationary member and the movable rack. Moreover, while a clevis has been shown for the purpose of permitting the jaws to rotate for opening and closing, it will be understood that a set of jaws may be used which do not require rotation for opening and closing. For example, as disclosed in co-owned application U.S. Ser. No. 08/440,326, elastic jaws can be used. Such jaws are closed and opened by the use of a cylinder coupled to the distal end of either the coil or the control wire, which moves distally over the jaws and proximally off of the jaws to move the jaws from an open position to a close position and back to an open position. While the elastic jaws will not rotate about an axis, it will nevertheless be understood that the tooth arrangement presently disclosed can be adapted for their use, such that the teeth on the jaws can mesh substantially simultaneously. In addition, while a monopolar cauterization plug has been shown to be conductively coupled to the coil, it will be appreciated that a bipolar configuration can also be used wherein a cauterization plug has bipolar connectivity to forceps jaws which are insulated from one another at the proximal end of the jaws. Conversely, the endoscopic biopsy forceps instrument may also have no cautery ability. It will therefore be appreciated by those skilled in the art that yet other modifications could be made to the provided invention without deviating from its spirit and scope as so claimed.

We claim:

1. An endoscopic biopsy forceps jaw assembly for use with an endoscopic biopsy forceps instrument where the endoscopic biopsy forceps instrument has a tubular member with a control member extending therethrough and actuating means coupled to the proximal ends of the tubular member and control member for reciprocally moving the control member axially through the tubular member, said endoscopic biopsy forceps jaw assembly comprising:

a pair of opposed first and second jaws, each of said jaws having a hollow jaw cup having a proximal end, a distal end, and a plurality of teeth, said teeth increasing in height as said teeth approach said distal end of said jaw cup, wherein said jaw assembly is coupled to the distal end of the control member and the tubular member, and reciprocal movement of the control member relative to the tubular member operates to move said jaws from a first open position into a second closed position.

2. An endoscopic forceps jaw assembly according to claim 1, wherein:

said plurality of teeth of said opposed first jaw are arranged in a first array and said plurality of teeth of said opposed second jaw are arranged in a second array such that said teeth of said first array closely and substantially simultaneously mesh with said teeth of said second array as said forceps jaw assembly is moved from said first open position into said second closed position.

3. An endoscopic forceps jaw assembly according to claim 2, wherein:

a first tooth of said array has a distally adjacent tooth 10% taller than said first tooth.

4. An endoscopic jaw assembly according to claim 3, wherein:

said teeth of said array each have peaks and valleys and said peaks fall along a first plane and said valleys fall along a second plane.

5. An endoscopic jaw assembly according to claim 1, wherein:

said first jaw further includes a first transverse mounting bore and said height of each of said plurality of teeth of said jaw cup of said first jaw is approximately proportional to the distance of each of said plurality of teeth from said first transverse mounting bore, and said second jaw further includes a second transverse mounting bore and said height of each of said plurality of teeth of said jaw cup of said second jaw is approximately proportional to the distance of each of said plurality of teeth from said second transverse mounting bore.

6. An endoscopic biopsy forceps jaw according to claim 2, wherein:

said first array of teeth includes first teeth on a first side of each of said jaw cups, and second teeth on a second side of each of said jaw cups, said first teeth and said second teeth being offset by one half pitch relative to each other.

7. An endoscopic biopsy forceps jaw according to claim 1, wherein:

said plurality of teeth are triangular-shaped.

8. An endoscopic biopsy forceps jaw according to claim 1, wherein:

said jaws are electrically conductive.

9. An endoscopic biopsy forceps instrument, comprising:

a) a tubular member having a proximal end and a distal end;

b) a control member having a proximal end and a distal end and extending through said tubular member;

c) actuating means coupled to said proximal ends of said tubular member and said control member for moving said control member axially and relative to said tubular member; and d) a jaw assembly coupled to said control member and said tubular member and having articulating and opposed first and second jaws, each of said jaws having a hollow jaw cup having a proximal end, a distal end, and a plurality of teeth, said teeth increasing in height as said teeth approach said distal end of said jaw cup, wherein said opposed first and second jaws are moved from a first open position into a second closed position in response to movement of said control member relative to said tubular member.

10. The endoscopic forceps instrument of claim 9, further comprising:

a clevis means at said distal end of said tubular member for coupling said jaw assembly to said tubular member.

11. An endoscopic forceps instrument according to claim 9, wherein:

said plurality of teeth of said opposed first jaw are arranged in a first array and said plurality of teeth of said opposed second jaw are arranged in a second array such that said teeth of said first array closely and substantially simultaneously mesh with said teeth of said second array as said forceps jaw assembly is moved from said first open position into said second closed position.

12. An endoscopic forceps instrument according to claim 9, wherein:

a first tooth of said array has a distally adjacent tooth 10% taller than said first tooth.

13. An endoscopic forceps instrument according to claim 12, wherein:

said teeth of said array each have peaks and valleys and said peaks fall along a first plane and said valleys fall along a second plane.

14. An endoscopic forceps instrument according to claim 10, wherein:

said first jaw further includes a first transverse mounting bore and said height of each of said plurality of teeth of said jaw cup of said first jaw is approximately proportional to the distance of each of said plurality of teeth from said first transverse mounting bore, and said second jaw further includes a second transverse mounting bore and said height of each of said plurality of teeth of said jaw cup of said second jaw is approximately proportional to the distance of each of said plurality of teeth from said second transverse mounting bore.

15. An endoscopic biopsy forceps instrument according to claim 11, wherein:

said first array of teeth includes first teeth on a first side of each of said jaw cups, and second teeth on a second side of each of said jaw cups, said first teeth and said second teeth being offset by one half pitch relative to each other.

16. An endoscopic biopsy forceps instrument according to claim 9, wherein:

said plurality of teeth are triangular-shaped.

17. An endoscopic forceps instrument according to claim 9, further comprising:

e) an insulative sheath around said tubular member; and f) connector means for coupling said coil to an electrocautery voltage supply, wherein said jaws are electrically conductive and said tubular member is electrically conductive.

* * * * *